United States Patent
Storup et al.

(10) Patent No.: US 12,064,365 B2
(45) Date of Patent: Aug. 20, 2024

(54) STRUCTURE COMPRISING STACKABLE LAYERS

(71) Applicant: Ossur Iceland ehf, Reykjavik (IS)

(72) Inventors: Martin Lund Storup, Reykjavik (IS); Andrew Bache, Reykjavik (IS); Christophe Guy Lecomte, Reykjavik (IS); Arinbjorn Clausen, Reykjavik (IS); Larus Gunnsteinsson, Reykjavik (IS); Felix Starker, Reykjavik (IS); Ragnar Örn Gunnarsson, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 79 days.

(21) Appl. No.: 16/026,181

(22) Filed: Jul. 3, 2018

(65) Prior Publication Data

US 2019/0000659 A1   Jan. 3, 2019

Related U.S. Application Data

(60) Provisional application No. 62/528,282, filed on Jul. 3, 2017.

(51) Int. Cl.
*A61F 5/01* (2006.01)
*A61F 2/50* (2006.01)
(Continued)

(52) U.S. Cl.
CPC .............. *A61F 5/0106* (2013.01); *A61F 2/50* (2013.01); *A61F 5/01* (2013.01); *A61F 5/05858* (2013.01);
(Continued)

(58) Field of Classification Search
CPC ...... A61F 2002/5016; A61F 2002/5018; A61F 200/00; A61F 2/50; A61F 5/00; A61F 5/01; A61F 5/05833; B32B 7/08; B32B 27/08

See application file for complete search history.

(56) References Cited

U.S. PATENT DOCUMENTS

| 4,556,439 A | 12/1985 | Bannink, Jr. |
| 4,750,905 A | 6/1988 | Koeneman et al. |

(Continued)

FOREIGN PATENT DOCUMENTS

| EP | 0505738 A1 | 9/1992 |
| EP | 2487024 A1 | 8/2012 |

(Continued)

OTHER PUBLICATIONS

International Search Report and Written Opinion from PCT Application No. PCT/US2018/040684, Sep. 27, 2018.

*Primary Examiner* — Maria V Ewald
*Assistant Examiner* — Daniel P Dillon
(74) *Attorney, Agent, or Firm* — Workman Nydegger

(57) ABSTRACT

A structure assembled by first and second stackable layers having properties allowing for the first and second stackable layers to be shaped into at least first and second different shapes, and at least one fastener to releasably secure the first and second stackable layers together in one of the at least first and second shapes in a semi-rigid or rigid, and unitary construction. The first and second stackable layers are secured into one of the at least first and second shapes by the at least one fastener to form a semi-rigid or rigid, and unitary construction.

15 Claims, 12 Drawing Sheets

(51) Int. Cl.
*A61F 5/058* (2006.01)
*B32B 7/08* (2019.01)
*B32B 27/08* (2006.01)

(52) U.S. Cl.
CPC ............... *B32B 7/08* (2013.01); *B32B 27/08* (2013.01); *A61F 2002/5016* (2013.01); *A61F 2002/5056* (2013.01); *B32B 2535/00* (2013.01)

(56) References Cited

U.S. PATENT DOCUMENTS

| | | | |
|---|---|---|---|
| 5,064,439 A | 11/1991 | Chang et al. | |
| 5,151,277 A | 9/1992 | Bernardon et al. | |
| 5,181,930 A | 1/1993 | Dumbleton et al. | |
| 6,106,646 A | 8/2000 | Fairbanks | |
| 7,550,189 B1* | 6/2009 | McKnight | B32B 3/10 |
| | | | 148/563 |
| 8,057,206 B1 | 11/2011 | Mcknight | |
| 8,201,371 B2* | 6/2012 | Kismarton | B29C 66/45 |
| | | | 52/309.16 |
| 8,592,531 B2 | 11/2013 | Thomas et al. | |
| 2010/0161076 A1* | 6/2010 | Pallari | A43B 13/183 |
| | | | 700/98 |
| 2012/0041567 A1* | 2/2012 | Cornell | A61F 2/7812 |
| | | | 623/33 |
| 2012/0310126 A1 | 12/2012 | Bureau et al. | |
| 2013/0018294 A1* | 1/2013 | Jones | A61F 5/30 |
| | | | 602/27 |
| 2014/0277584 A1* | 9/2014 | Hurley | B29C 70/42 |
| | | | 623/33 |
| 2015/0369325 A1* | 12/2015 | Bureau | F16F 9/04 |
| | | | 428/35.4 |
| 2016/0038311 A1* | 2/2016 | Gonzalez | A61F 2/6607 |
| | | | 623/55 |
| 2017/0304082 A1* | 10/2017 | Lindhe | A61F 2/66 |
| 2018/0296373 A1* | 10/2018 | Granz | A61F 2/7812 |

FOREIGN PATENT DOCUMENTS

| | | |
|---|---|---|
| WO | 9614196 A1 | 5/1996 |
| WO | 02094565 A1 | 11/2002 |
| WO | 2016100170 A1 | 6/2016 |

* cited by examiner

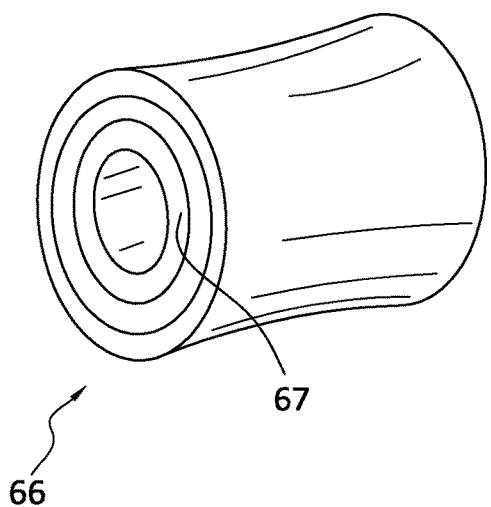
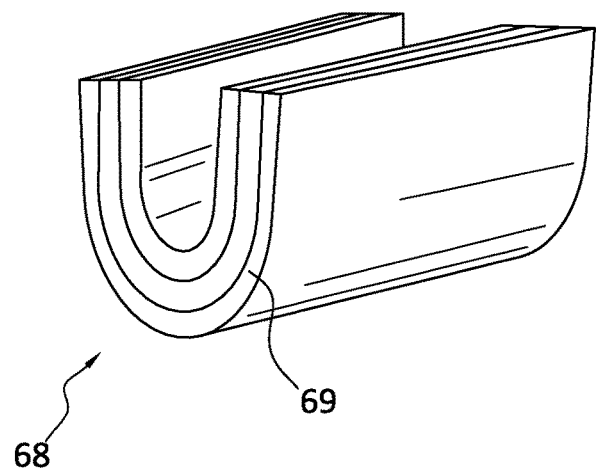
FIG. 10a    FIG. 10b
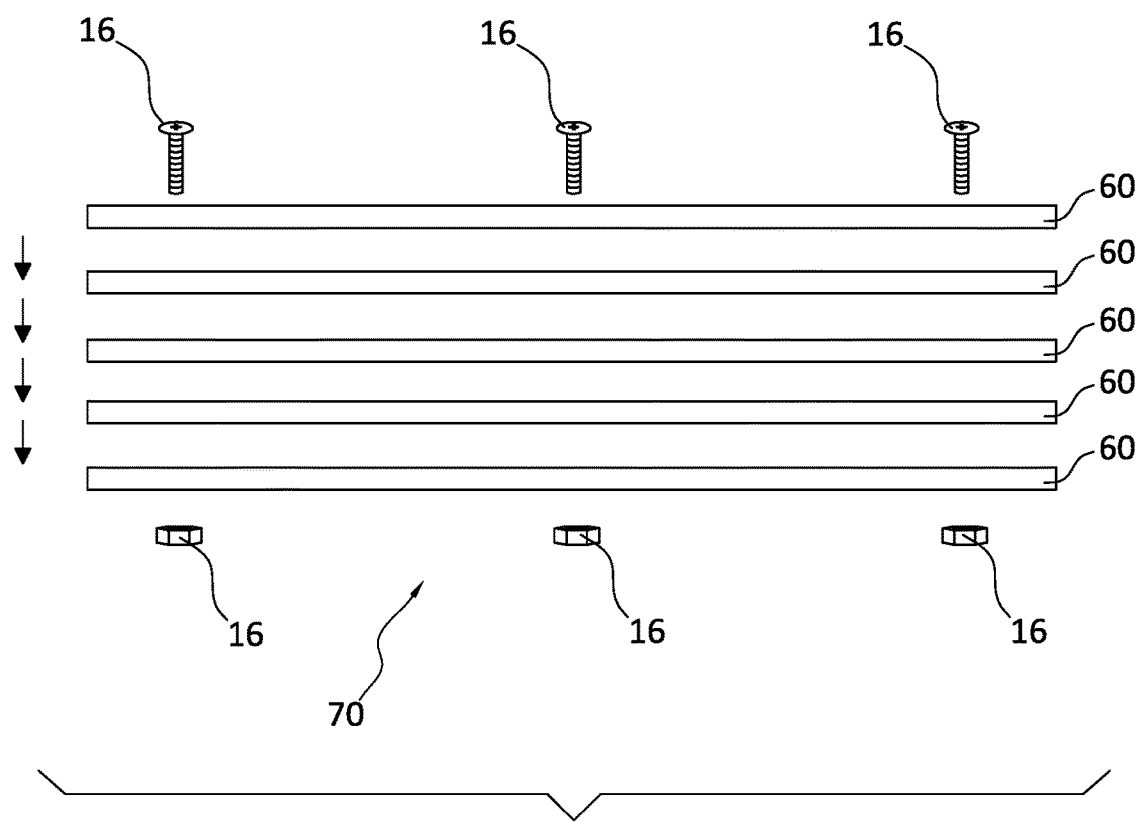
FIG. 11

STRUCTURE COMPRISING STACKABLE LAYERS

FIELD OF THE DISCLOSURE

The disclosure relates to assembled structures comprising at least two stackable layers and at least one fastener so the assembled structures are substantially rigid, the at least two stackable layers being individually adjustable in shape.

BACKGROUND

A rigid structure is advantageous for various uses, for example in scenarios such as consumer products, furniture, manufacturing implementations, medical devices, and transportation implements. A rigid structure may advantageously offer structural support, give shape to a product or device, or be an integral component of a device in which its rigid properties may be advantageous for providing strength, shape, and support, among other benefits.

There is a problem, however, of rigid structures being difficult to adjust in shape as needed. The rigid structure may require adjustment if its shape changes due to mechanical stresses, tensions, or creep, or large temperature changes causing deformation. An object or device for which the rigid structure was designed to fit or to be complementary may change in size or shape, rendering the rigid structure obsolete or ineffective.

A rigid structure may not be properly shapeable at the time of mass manufacturing; it must be customized to individual end uses, dispositions, or users. A rigid structure may need to fit the specific dimensions unique to each disposition which dimensions are not easily ascertainable at the time of manufacture. When the rigid structure comprises a synthetic material such as carbon fiber, it can be difficult to customize the rigid device to the required dimensions absent costly and time-consuming custom manufacturing because of the rigid structure's rigid properties. A rigid structure may be difficult to adjust without specialized machinery and/or complicated technical processes.

A rigid structure may need to assume a different shape than its original shape based on new or different uses for the rigid structure. A standard shape may be provided that can be modified for a particular shape. Adjustment of the shape of the rigid structure to accommodate the changes in size or shape can be very difficult or cost-prohibitive, owing to the rigid properties of the rigid structure.

The rigid structure may need to support various attachments, which may be difficult to add or remove during the normal course of use as needs change. It may be difficult to incrementally vary the rigidity of the rigid structure as needed or desired.

There is need for a rigid structure that can be easily and effectively adjusted in shape as needed or desired.

SUMMARY

The problem of semi-rigid or rigid structures being difficult to adjust in shape as needed or desired is solved according to embodiments of the disclosure by providing an assembled structure comprising at least two stackable layers releasably secured into a position by at least one fastener. The at least two stackable layers have properties so the at least two stackable layers are individually adjustable in shape when not secured into the position by the at least one fastener, and so when the at least two stackable layers are releasably secured into position by the at least one fastener, the assembled structure is at least semi-rigid and has a unitary construction.

The assembled structure advantageously allows a user to adjust as desired the shape of the assembled structure by disassembling the assembled structure by releasing the at least one fastener, adjusting each of the at least two stackable layers into a desired shape, and then re-assembling the assembled structure by releasably securing the at least two stackable layers with the at least one fastener.

The unitary construction simplifies the parts and offers a generally uniformly structured frame for supporting a load, in that it can be rendered lighter and more rigid than a construction that includes separate components attached to or provided in combination with a frame. Indeed, the unitary construction can form a space frame in that it is formed as a three-dimensional skeletal frame including a series of struts integrally formed together by a plurality of layers. The loads exerted on the struts of the unitary construction can be tensile or compressive, but when constructed in the assembled structure, the struts do not bend.

The assembled structure, including the at least two stackable layers and the at least one fastener, may be configured in size and shape to support various attachments, materials, or components, to function as part of a device, structure, or machine. The assembled structure is advantageous in that it can be disassembled and re-assembled to quickly and easily add or remove attachments or components as needed or desired.

A plurality of assembled structures according to the disclosure, including the at least two stackable layers and the at least one fastener, may be configured in size and shape to be complementary to a structure, device, or machine. One or more assembled structures in a representative embodiment of the disclosure may function as semi-rigid or rigid structural elements in a device.

In a representative embodiment, the assembled structure may comprise discrete frame elements usable to be shaped to an individual user's anatomy, such as for an orthopedic or prosthetic device. The assembled structure advantageously allows a clinician or practitioner to shape at least two stackable layers suitable for use as a frame element to a user's specific dimensions and assemble the at least two stackable layers into a semi-rigid or rigid element, all while avoiding the use of specialized machinery, such as vacuums, adhesives, and/or heating and cooling elements, any of which may be adverse to a human patient's comfort and health when the assembled structure is applied over a user's anatomy.

Additional features and advantages of the disclosure will be in the description that follows, and in part will be obvious from the description, or may be learned by the practice of the disclosure. The features and advantages of the disclosure may be realized and obtained with the instruments and combinations particularly pointed out in the appended claims. These and other features of the present disclosure will become more apparent from the following description and appended claims, or may be learned by the practice of the disclosure as set forth.

BRIEF DESCRIPTION OF THE DRAWINGS

FIG. 3b is an elevational view of the assembled structure functioning as part of the ankle foot orthosis of FIG. 3a.

FIG. 10a is a profile view of an assembled structure comprising stackable layers in a tubular shape.

FIG. 10b is a profile view of an assembled structure comprising stackable layers in a U-shape.

FIG. 11 is an exploded view of an assembled structure.

Figure 1:
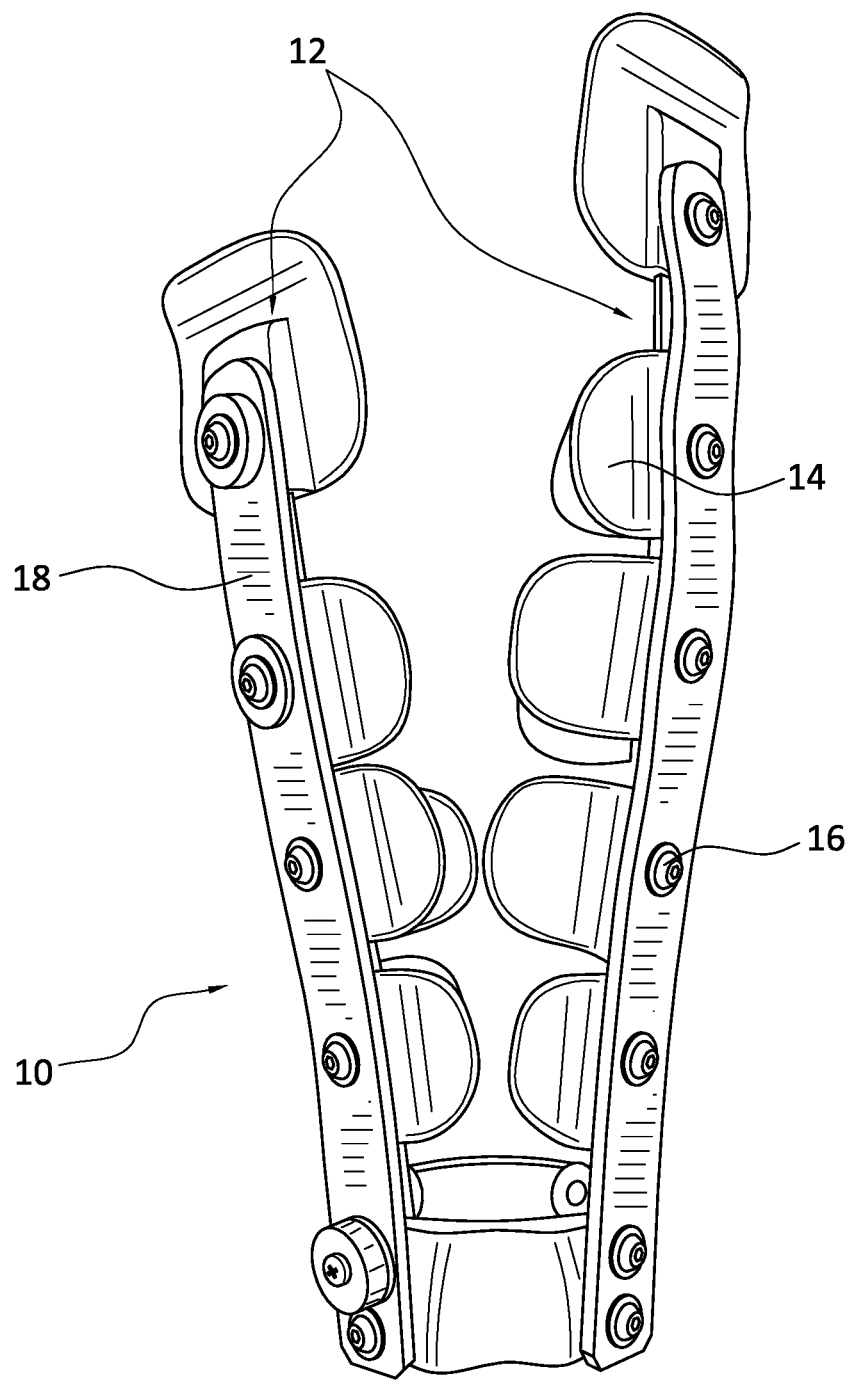
FIG. 1 is a perspective view of a representative embodiment of a plurality of assembled structures functioning as part of a prosthetic socket.

The drawing figures are not necessarily drawn to scale, but instead are drawn to provide a better understanding of the components, and are not intended to be limiting in scope, but to provide exemplary illustrations. The figures illustrate exemplary configurations of an assembled structure comprising stackable layers, and in no way limit the configurations of an assembled structure comprising stackable layers and components according to the present disclosure.

DETAILED DESCRIPTION OF VARIOUS EMBODIMENTS

For further ease of understanding the representative embodiments of an assembled structure comprising stackable layers, these terms may be used with the features of the exemplary embodiments.

The term "layer" refers to a discrete unit of material as opposed to an integrated and un-releasable stratum of a larger whole. The term "stackable" has its ordinary meaning and refers to an ability to be assembled coextensively with like materials in layers. The term "fastener" has its ordinary meaning and refers to a device, material, or implement that functions to secure materials or components in place. For example, the fastener may be any one or a combination of nuts and bolts, adhesive material, magnets, tape, bands, rings, clips, hook and loop fastener, thermoplastic material, resin, glue, clamps, slide fasteners, buttons, pins, buckles, string, wire, rope, or belts.

It will be understood that the usage of ordinals, such as "first," "second," and etc. are nominally used as associative denotations, but are not necessarily provided to denote spatial location. Rather, the ordinal merely associates one element with another element, or distinguishes one element from another element.

The terms "rigid" and "flexible" are used herein to distinguish characteristics of portions of the brace. The term "rigid" should denote that the frame is generally devoid of flexibility. Within the context of frame members that are "rigid," it should indicate that they may break if bent with sufficient force. The term "flexible" should denote that features are capable of repeated bending. Semi-rigid connotes rigidity to some degree or in some parts but not necessarily completely rigid, with the possibility of some degree of flexibility. The term "resilient" is used to qualify such flexible features as generally returning to the initially molded shape with permanent deformation. The term "substantial" and variants thereof takes on the ordinary meaning of being "for the most part" or to a "great or significant extent."

While the disclosure is susceptible to various modifications and alternative constructions, certain illustrative embodiments are in the drawings and are described below. It should be understood, however, there is no intention to limit the disclosure to the embodiments disclosed, but on the contrary, the intention covers all modifications, alternative constructions, combinations, and equivalents falling within the spirit and scope of the disclosure.

Reference characters are provided in the claims for explanatory purposes only and are not intended to limit the scope of the claims or restrict each claim limitation to the element in the drawings and identified by a reference character.

In a representative embodiment, a plurality of assembled structures form struts in a prosthetic socket. The prosthetic socket is an important component of a prosthetic device because it carries the body weight of a user, and if improperly and/or not custom configured to the user's precise dimensions, can cause discomfort for the user. A poorly fitting socket can create pressure points leading to soreness and blisters, cause soft tissue damage, and compromise mobility.

A user's dimensions can change over time; a user may gain or lose weight, swelling can occur and/or recede in a limb stump, and/or a user's weight distribution may shift. However, most prosthetic sockets are permanently formed to a customized shape that is static, and does not account for shape and volume fluctuations of the residual limb. In prosthetic sockets that comprise no plurality of assembled structures serving as struts, a change in a user's dimensions therefore requires ordering, manufacturing, and customizing entirely new sockets, at great cost to the user, or engaging in costly and inconvenient adjustment procedures for the existing sockets. In situ adjustments of such devices may require the aid of specialized machinery and/or using complex technical processes, requiring the time and attention of skilled individuals to carry out properly. This can greatly increase a user's costs and inconvenience associated with adjustments of the device.

A plurality of assembled structures serving as adjustable struts is a desirable feature of prosthetic sockets because of the high cost and importance of proper configuration of the struts in a prosthetic socket; an adjustable prosthetic socket could advantageously adapt to the user's dimensions while avoiding the high costs and inconvenience of creating new sockets each time a user's dimensions change. A plurality of assembled structures functioning as adjustable struts would also simplify fitting a socket to a new user. A device comprising a plurality of assembled structures as struts advantageously avoids the need to use specialized machinery and/or using complex technical processes to properly fit or adjust a socket to a user's dimensions, avoiding the cost and inconvenience to the user of the same.

A plurality of assembled structures allows a user or practitioner/clinician to easily and inexpensively adjust the dimensions of the prosthetic socket by disassembling the plurality of assembled structures which form the struts by releasing the at least one fastener, adjusting each of the stackable layers into a desired shape to accommodate the user's changed dimensions, and then re-assembling the assembled structure by releasably securing the at least two stackable layers with the at least one fastener. This eliminates the need for a user to obtain an entirely new socket and avoids permanently altering the struts, and this may be done without sacrificing the rigidity and structural support required by the struts of a prosthetic socket, because the stackable layers have properties so the assembled structures are at least semi-rigid when assembled. The stackable layers may be initially individually flexible, prior to be being placed in the assembled structure, and may be resilient once the assembled structure is disassembled so that the stackable layers generally revert to their initial, predetermined shape, even after having been placed in the assembled structure.

FIG. 1 illustrates a representative embodiment of a plurality of assembled structures 12 functioning as part of a prosthetic socket 10. At least one fastener 16 releasably secures at least two stackable layers 18 to form an assembled structure 12. The plurality of assembled structures 12 are additionally configured in size and shape to support cuff attachments 14. The individual assembled structures 12 are at least semi-rigid or substantially rigid, owing to properties of the at least two stackable layers 18, which when secured by the at least one fastener 16 to form the assembled structure 12 function to provide required rigidity and support to the prosthetic socket 10.

The embodiment of FIG. 1 is desirable because the plurality of assembled structures 12 provide the unique advantage of being adjustable in shape, for example if a user's residual limb changes in size or shape. A user or clinician may simply disassemble the assembled structure 12, adjust the shape of the at least two stackable layers 18 to the desired shape, and then reassemble the assembled structure 12 by securing the at least two stackable layers 18 with the at least one fastener 16.

The assembled structure constitutes a unitary construction, frame or configuration by forming a single or main structure to which other components may be attached and is a load-carrying unit that can singularly handle loads. In the example of the prosthetic socket, while the assembled structure includes multiple components, when fastened, the multiple components harmoniously work together to form a unitary frame that is load bearing despite the multiple components. The assembled structure sustains a certain level of rigidity, such as being semi-rigid or substantially rigid meaning that while not completely rigid prior to load bearing, the assembled structure is sufficiently rigid to loading without deformation during use, thereby maintaining its shape. Likewise, the assembly structure may be completely rigid, either before or after load bearing.

Figure 2A:
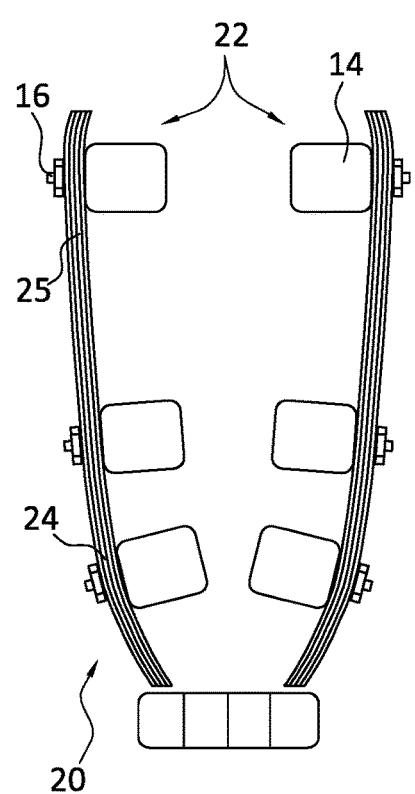
FIG. 2a is a schematic view of a representative embodiment of a plurality of assembled structures according to the disclosure functioning as part of a prosthetic socket and having a first shape.
Figure 2B:
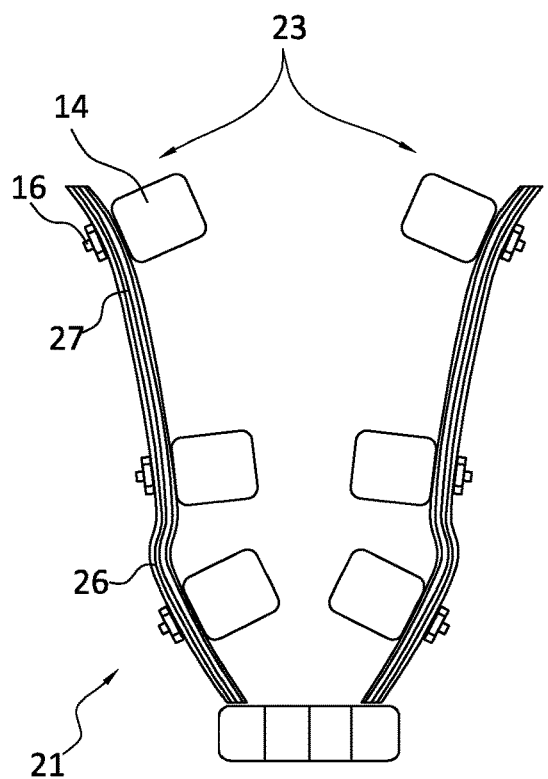
FIG. 2b is a schematic view of the representative embodiment of FIG. 2a having a second shape.

FIGS. 2a and 2b illustrate a representative embodiment of a plurality of assembled structures 12 according to the disclosure functioning as part of prosthetic sockets 20, 21 and having first (FIG. 2a) and second (FIG. 2b) shapes for different configurations of the prosthetic sockets 20, 21. FIG. 2a shows a prosthetic socket in a first configuration 20 incorporating a plurality of assembled structures in a first shape 22. The assembled structures in a first shape 22 receive their shape from first and second curvatures 24, 25. FIG. 2a shows a prosthetic socket in a second configuration 21 incorporating assembled structures in a second shape 23. The assembled structures in a second shape 23 receive their shape from third and fourth curvatures 26, 27.

The prosthetic socket in a first configuration 20 may be easily, inexpensively, and quickly adjusted to become the prosthetic socket in a second configuration 21 by adjusting each one of the plurality of assembled structures in a first shape 22 into the assembled structures in a second shape 23 according to a method described in the disclosure. This may be necessary if the limb of a user of the prosthetic socket in a first configuration 20 changes in size or shape during treatment or recovery (such as through swelling), if the user's weight or weight distribution changes, or if the prosthetic device in a first configuration 20 undergoes mechanical stress, tension, or creep, any one or a combination of which may render the prosthetic socket in a first configuration 20 ineffective, uncomfortable, or obsolete. The user or a practitioner/clinician may adjust the shape of the assembled structures in a first shape 22 to a more desirable shape to accommodate the change in dimensions of the user, for example to the shape of the assembled structures in a second shape 23. This is advantageous because existing prosthetic sockets are custom manufactured for each individual user, and require the assistance of a trained prosthetist and frequently the use of specialized machinery and/or complex technical processes to properly fit to the residual limb; acquiring a new prosthetic socket each time a user's dimensions change due to the above factors is inconvenient and prohibitively expensive for most users. The use of assembled structures in a prosthetic socket to easily adjust the configuration of the socket as needed is desirable as it eliminates the need for a user to incur the costs and inconveniences of ordering and acquiring a new prosthetic socket.

As in FIG. 1, the assembled structures in a first shape 22 and the assembled structures in a second shape 23 have at least one fastener 16 and may be configured in size and shape to support cuff attachments 14.

Using assembled structures to form struts in a prosthetic socket therefore provides numerous advantages to a user, specifically in that the user and/or a practitioner/clinician may easily, quickly, and inexpensively adjust the shape of the struts to accommodate changes in a user's dimensions without sacrificing the required and structural support required of prosthetic sockets. The ability to easily accommodate the changes in a user's dimensions also provides for better comfort and use of the prosthetic socket, as the pressure points, discomfort, soft tissue breakdown, and loss of mobility that result from poorly-fitting prosthetic sockets are avoided.

An assembled structure may also form a semi-rigid or rigid strut in an ankle foot orthosis to treat foot drop. Foot drop is a condition wherein a person has difficulties with raising their toes or their foot from their ankle, causing their foot to point downward, making walking and other activities difficult. Ankle foot orthoses to treat foot drop typically comprise a foot plate to support the foot in a raised position attached to a strut that extends along and attaches at a user's lower leg. In such orthoses, the strut must have rigid properties allowing for proper support of the foot and leg, but must also be customizable to the dimensions of a user's leg for good fit, comfort, and sustained use.

An assembled structure serving as the strut of an ankle foot orthosis is advantageous because it allows a clinician to ensure that the strut is properly configured to the user's unique dimensions by adjusting the individual layers without sacrificing necessary structural support. As with the prosthetic socket example, the user's leg may change in shape over time, such as through weight gain or loss, or through swelling, or the rigid strut may partially deform due to mechanical stresses. The required dimensions of the orthosis may also change based on different stages of a user's recovery or therapy. An assembled structure mitigates these challenges by allowing a clinician or user to adjust the shape of the assembled structure without obtaining a new custom orthosis or using specialized machinery and/or complex technical processes to adjust the shape of an existing orthosis.

Figure 3A:
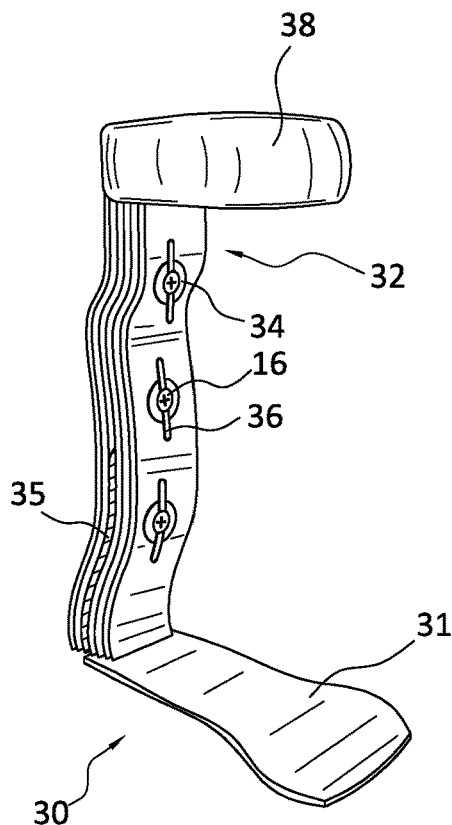
FIG. 3a is a profile view of another representative embodiment of an assembled structure functioning as part of an ankle foot orthosis.
Figure 3B:
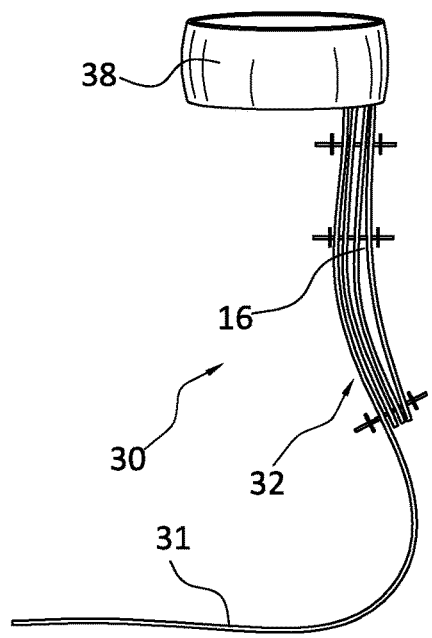

Turning now to FIGS. 3a and 3b, an assembled structure 32 serving as a strut in an ankle foot orthosis 30 is shown in profile and elevational views, respectively. The assembled structure 32 can be configured in shape to comfortably fit the leg of a user. The assembled structure comprises apertures 36 and fasteners 16, and a plurality of recesses 34 in at least one of the stackable layers of the assembled structure 32, which are configured in size and shape to enhance comfort by receiving the fasteners 16 so the fasteners 16 do not protrude beyond the top layer of the assembled structure 32.

A foot plate 31 is attached to a distal portion of the assembled structure 32 by an attachment extension 35 attaching to at least one aperture 36, which along with the fasteners 16 may support various attachments to the foot plate. For example, a calf cuff 38 attaches to the assembled structure 32 at a proximal portion of the assembled structure 32.

The assembled structure 32 advantageously allows a practitioner/clinician to adjust the configuration of the assembled structure 32 to better fit the dimensions of an individual user for optimal comfort and mobility without sacrificing required rigidity and support. As in the prosthetic sockets 20, 21 described above, the ability to adjust the configuration of the assembled structure 32 in response to changes in the dimensions of the user, different stages of therapy and recovery, or changes to the dimensions of the ankle foot orthosis 30 during use, is desirable to reduce the cost and inconvenience incurred by a user in obtaining a new custom ankle foot orthosis in response to each such change or having their current orthosis professionally and/or permanently adjusted, often through the expensive and inconvenient use of specialized machinery and/or complex technical processes. In this example, any necessary adjustments can advantageously be done quickly and easily by hand in situ.

Figure 4A:
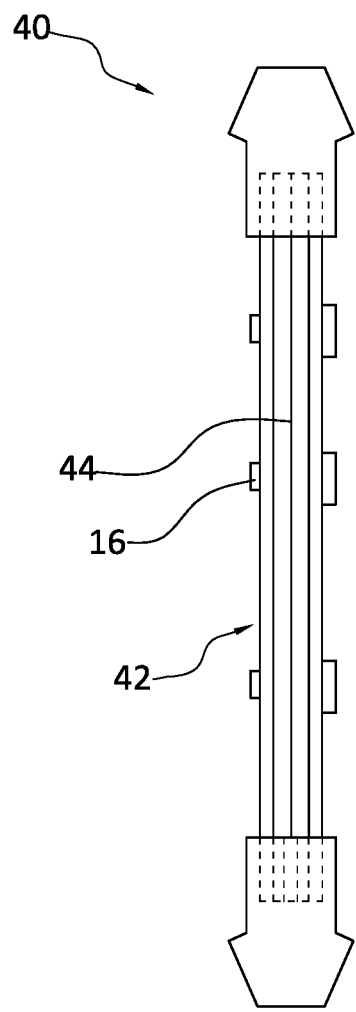
FIG. 4a is an elevational view of another representative embodiment of an assembled structure functioning as a pylon for a prosthetic foot in a straight configuration.
Figure 4B:
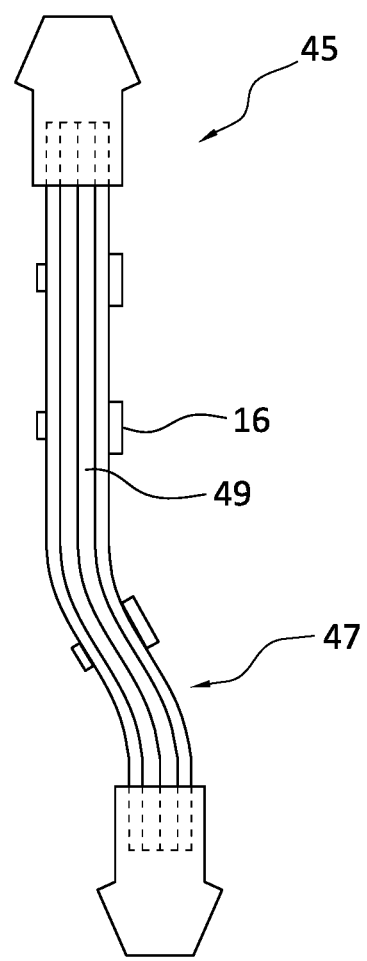
FIG. 4b is an elevational view of an assembled structure functioning as a pylon for a prosthetic foot in a bent configuration.

Turning now to the embodiment of FIGS. 4a and 4b, an assembled structure in a straight configuration 42 is shown serving as a pylon in a straight configuration 40 for a prosthesis. A pylon connects a prosthetic socket to a prosthetic foot, and must be capable of enduring not only transverse forces but also axial forces from supporting the weight of a user. The assembled structure in a straight configuration 42 comprises at least two stackable layers in a straight configuration 44 secured by at least one fastener 16, and advantageously provides rigidity and support under a plurality of forces, including transverse and axial, while also allowing a user or practitioner to easily and quickly adjust the shape of the pylon in a straight configuration 40.

FIG. 4b shows an assembled structure in a bent configuration 47 serving as a pylon in a bent configuration 45 for a prosthesis. A pylon 40, 45 may require adjustment in configuration to better accommodate the weight distribution of a user, and the assembled structures 42, 47 reduce costs and inconveniences incurred by users as the shape of the pylons 40, 45 may be adjusted by adjusting the shape of the assembled structures 42, 47.

The user or practitioner follows a method in the disclosure of disassembling the assembled structure in a straight configuration 42 by releasing the at least one fastener 16, shapes the at least two stackable layers in a straight configuration 44 into a desired shape such as the at least two stackable layers in a bent configuration 49, and then re-assembles the at least two stackable layers in a bent configuration 49 with the at least one fastener 16 into the assembled structure in a bent configuration 45. This method advantageously mitigates the need for remote manufacturing or the cost and inconvenience of presenting the pylon 40, 45 to a practitioner for difficult adjustment, potentially requiring the use of specialized machinery and/or complex technical processes.

Figure 5A:
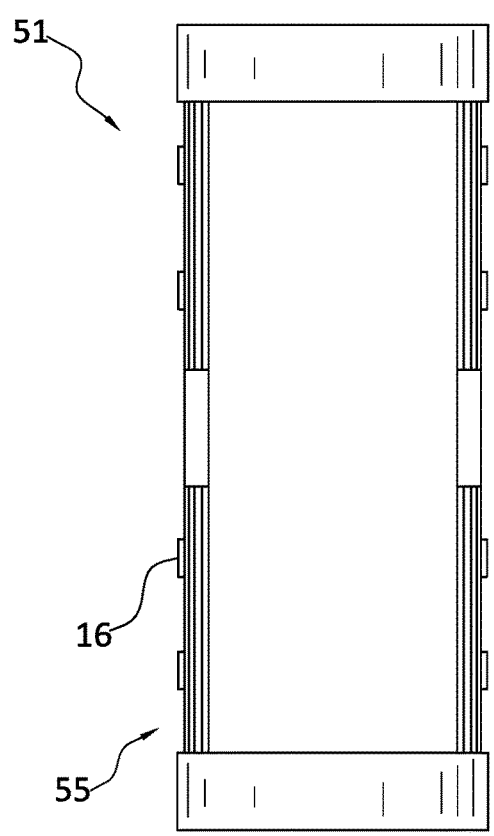
FIG. 5a is an elevational view of another representative embodiment of a plurality of assembled structures in a narrow configuration functioning as struts in a double hinged knee brace in a narrow configuration.
Figure 5B:
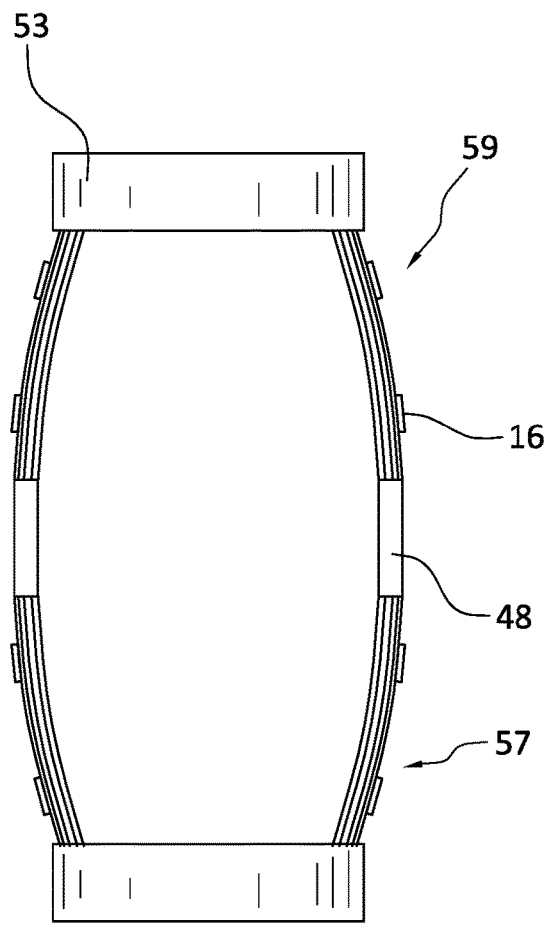
FIG. 5b is an elevational view of a plurality of assembled structures in a wide configuration functioning as struts in a double hinged knee brace in a wide configuration.

Turning now to FIGS. 5a and 5b, a plurality of assembled structures in a narrow configuration 55 serve as struts in a double hinged knee brace in a narrow configuration 51. The plurality of assembled structures in a narrow configuration 55 may be configured to support attachments such as leg cuffs 59 and hinges 48. Like other orthopedic and prosthetic devices, knee braces must closely conform to the dimensions of a user to be suitable and effective for treating ailments of the knee and leg. Because different users' dimensions vary in many specific ways that are not ascertainable when knee braces are manufactured, a knee brace comprising assembled structures is advantageous as it allows a practitioner to fine tune each brace to the needs of each user for optimal performance with no time-consuming and expensive custom manufacturing, which often may require the costly and inconvenient use of specialized machinery and/or complex technical processes.

FIG. 5a shows a double hinged knee brace in a narrow configuration 51 which may be suitable for some users, but for others the configuration in FIG. 5b may be more appropriate. The plurality of assembled structures in a narrow configuration 55 may advantageously be dis-assembled by releasing the at least one fastener 16, each stackable layer reshaped into the desired configuration, and then re-assembled into a plurality of assembled structures in a wide configuration 57 according to the method of the disclosure. A double hinged knee brace in a wide configuration 53 is easily, quickly, and affordably obtained to better suit certain users' dimensions.

The above representative embodiments indicate the advantages of the assembled structures in a plurality of prosthetic and orthopedic devices where rigidity is required to resist axial forces, transverse forces, and other forces but adjustability is also advantageous; the assembled structures could form struts, cuffs, or supports in calf pieces, spinal braces, shoulder braces, cervical collars, hand braces, or other devices where both rigidity and user-specific shape are required.

The assembled structure can also advantageously serve as a stay in a temporary splint for emergency medical treatment. For instance, an assembled structure may form a rigid stay in an elbow splint for broken bones or injured limbs. This advantageously allows emergency medical works to customize the configuration of the assembled structure to the specific dimensions of the user in situ, providing optimal immobilization and stabilization of the injured limb without having to transport unwieldy quantities of differently sized and shaped splints to accommodate the different sizes of potential patients. The assembled structure provides an advantage over using, for example, a malleable aluminum stay to perform a similar function because the assembled structure can quickly and reusably be adjusted to the required shape while providing incrementally varying degrees of rigidity and structural support by adding or removing stackable layers. The assembled structure also endures both transverse and axial forces while also resisting shear forces between the at least two stackable layers. The assembled structure is reusable because it may be repeatedly shaped to accommodate future patients, advantageously pressuring custom-sized equipment that emergency medical works must transport to any emergency and reducing waste from single use splints.

Figure 6:
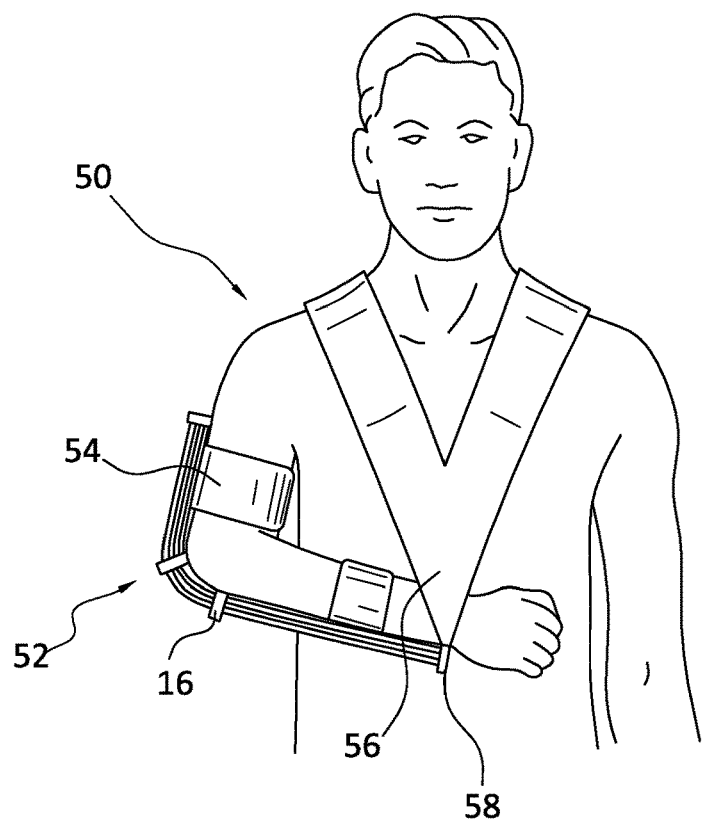
FIG. 6 is a schematic view of another representative embodiment of an assembled structure functioning as part of a temporary splint for an arm or shoulder injury.

FIG. 6 depicts a representative embodiment of an assembled structure 52 serving as a stay in a reusable temporary splint 50 for emergency situations. The assembled structure 52 is configured, in this embodiment, to fit the arm of a user at the elbow and along proximal and distal portions of the arm, preventing further injury by immobilizing the arm from flexing at the elbow. The at least one fastener 16 is shown in this embodiment as a bracket encircling the at least two stackable layers and securing the stackable layers in configuration. The assembled structure 52 is configured to support various attachments, including cuff attachment 54 and strap attachment 58.

This embodiment is advantageous because it allows a practitioner such as an emergency medical technician to easily and quickly adjust the assembled structure 52 by shaping the at least two stackable layers in situ to effectively brace and immobilize an injured limb according to the dimensions of a user, without having to transport an unwieldy amount of differently sized splints and braces to accommodate injured persons of various dimensions.

The assembled structure can also be permanently fixed into position by the at least one fastener. This is useful where, for example, a semi-rigid or rigid element must be custom-shaped for a user or device and the dimensions to which the semi-rigid or rigid element must be shaped may not be readily ascertainably. A clinician may need to provide a rigid crossbeam of a specific length and curvature for a knee brace, but the user's leg's precise dimensions may only be ascertainable in a clinical setting. Providing at least two stackable layers that may be easily, quickly, and permanently fixed into an assembled structure by a fastener with the precise configuration required in situ is highly desirable to reduce the costs and inconvenience of remotely manufacturing the rigid elements yet still provide requisite rigidity.

Figure 7:
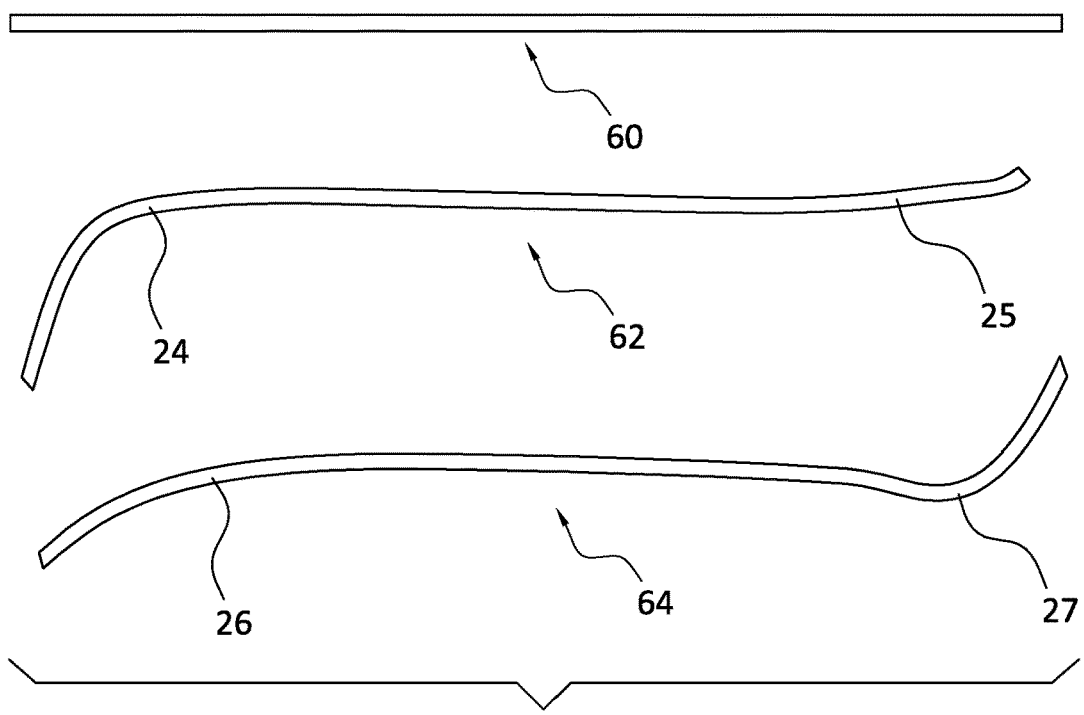
FIG. 7 is an elevational view of individual stackable layers.

Turning now to FIG. 7, a profile view of individual stackable layers having different shapes is given. A stackable layer before shaping 60, a stackable layer in a first shape 62 having first and second curvatures 24, 25, and a stackable layer in a second shape 64 having third and fourth curvatures 26, 27, are presented. Each of the stackable layers 60, 62, 64 has properties that allow the stackable layers 60, 62, 64 to be shaped into at least first and second shapes, and so when at least two stackable layers 60, 62, 64 are assembled into an assembled structure by at least one fastener 16, the assembled structure is at least semi-rigid or substantially rigid.

In an embodiment, the stackable layers 60, 62, 64 have properties allowing them to be repeatedly shaped. In another embodiment, the stackable layers 60, 62, 64 are sufficiently pliant to be shapeable by an unaided person. These properties enable the advantageous features of the assembled structures by enabling the assembled structures to be assembled, dis-assembled, and re-assembled, throughout their course of use, with different shapes and configurations as needed. These properties further allow individuals to shape the stackable layers 60, 62, 64 without having to incur the costs and inconveniences of remote and/or machine-aided manufacturing; rather, the stackable layers 60, 62, 64 can be adjusted quickly and easily by a person to adjust the shape of the assembled structure.

In another embodiment, the assembled structure comprises stackable layers 60, 62, 64 generally of uniform size and shape. This embodiment is advantageous because it allows for the assembled structures to have a minimized profile and surface area and maximized structural strength.

In another embodiment, the stackable layers 60, 62, 64 comprise a composite or polymeric material. For example, the stackable layers 60, 62, 64 may comprise one or more of carbon fiber, Kevlar®, glass fiber, plastic fiber, and/or strips of polymeric materials without fiber reinforcement. These materials may advantageously provide, in individual stackable layers 60, 62, 64, the requisite ability to be shapeable by an unaided person, but when stacked with at least one more layer, requisite rigidity. In another embodiment, the stackable layers 60, 62, 64 comprise a metallic material, for example layers of aluminum or steel. These materials may similarly provide shapeability in individual stackable layers and rigidity when the stackable layers are secured by at least one fastener into an assembled structure. In another embodiment, the assembled structure may comprise stackable layers comprising more than one type of material, for example outermost stackable layers comprising carbon fiber and inner stackable layers comprising plastic or rubber.

The stackable layers 60, 62, 64 may be substantially shaped as a thin, flat sheet. This property advantageously allows the stackable layers 60, 62, 64 to have the requisite ability to be shapeable by an unaided person. The stackable layers 60, 62, 64 may be substantially elongate, allowing the assembled structures to be suitable for numerous purposes, including to function as rigid supports in various devices, such as the representative embodiments described above.

The stackable layers 60, 62, 64 may be coextensive with each other; the stackable layers 60, 62, 64 may be arranged in offset, alternating, or woven patterns. These arrangements allow the assembled structures to serve many functions; for example, a woven pattern of stackable layers 60, 62, 64 may be advantageous in compliant surfaces, such as the backing and seat of a wheelchair. By providing an assembled structure of woven stackable layers 60, 62, 64, the backing and seat may be adjusted to fit the dimensions of the user without sacrificing required support.

Figure 8:
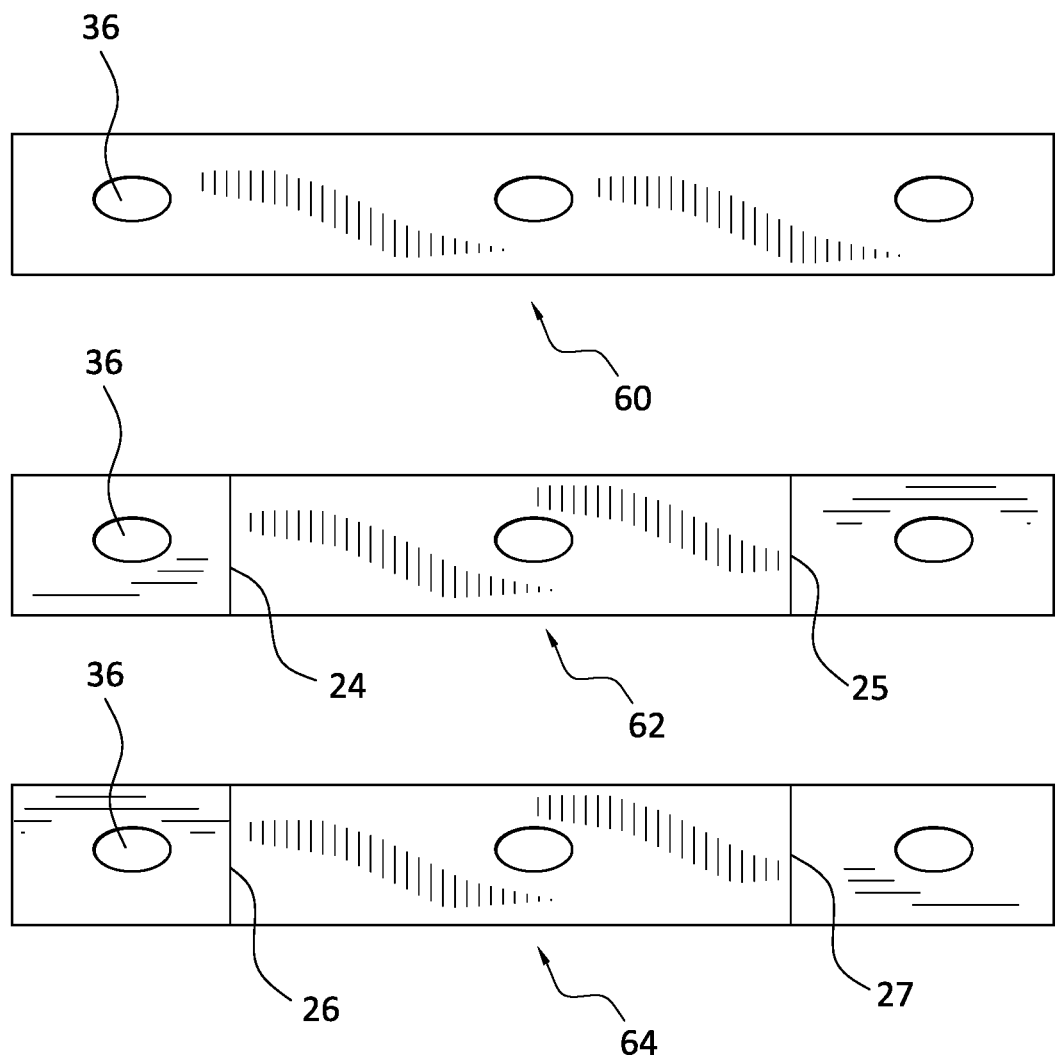
FIG. 8 is a plan view of the individual stackable layers illustrated in FIG. 7.

Turning now to FIG. 8, a top view of the individual stackable layers 60, 62, 64 having different shapes is presented. In an embodiment, the stackable layers 60, 62, 64 comprise the at least one aperture 36 configured in size and shape to receive the at least one fastener 16. Such an arrangement is advantageous as it allows the at least one fastener 16 to not protrude laterally from an assembled structure, minimizing bulk and difficulties in arranging one or more assembled structures 70 to function as part of a device, structure, or machine. First, second, third, and fourth curvatures 24, 25, 26, 27, as disclosed above, are visible in FIG. 8.

The at least one aperture 36 is substantially elongate to allow for some shifting between and/or among the individual stackable layers 60, 62, 64. The substantially elongate shape of the at least one aperture 36 provides a user and/or practitioner/clinician with an allowable margin of error in shaping each of the stackable layers 60, 62, 64 to a desired shape. The substantially elongate shape makes the at least one aperture 36 able to accommodate a range of different configurations of individual stackable layers 60, 62, 64, simplifying adjusting the shape of the assembled structure because a user or practitioner/clinician need not be precise in shaping each stackable layer 60, 62, 64.

Figure 9:
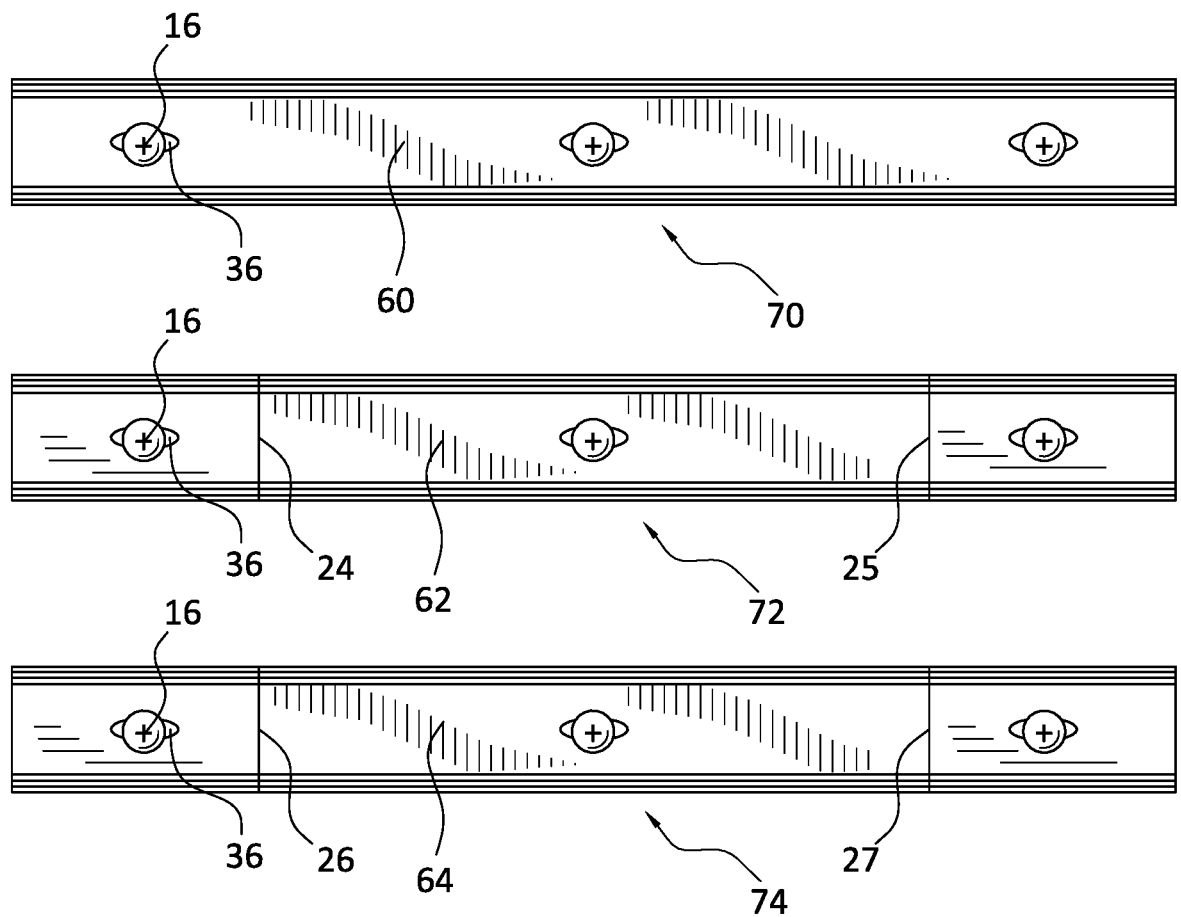
FIG. 9 is a plan view of the individual stackable layers illustrated in FIG. 7 assembled with at least one more stackable layer to form assembled structures.

Turning now to FIG. 9, a top view of assembled structures 70, 72, 74 comprising at least two stackable layers 60, 62, 64 and at least one fastener 16 is given. The at least one fastener 16 may be any device or material suitable for releasably securing the at least two stackable layers 60, 62, 64 in the assembled structure 70, 72, 74. The at least one fastener 16 may be any or a combination of nuts and bolts, adhesive material, tape, bands, rings, clips, hook and loop fastener, thermoplastic material, resin, glue, clamps, slide fasteners, buttons, pins, buckles, string, wire, rope, or belts.

In an embodiment, the at least one fastener 16 cooperates with the at least one aperture 36 to releasably secure the at least two stackable layers 60, 62, 64 in the assembled structures 70, 72, 74. The embodiments of FIGS. 7 and 8 use at least one fastener 16 of a nuts and bolts variety to releasably secure the at least two stackable layers 60, 62, 64 in the assembled structures 70, 72, 74. The at least one fastener 16 releasably may secure the at least two stackable layers 60, 62, 64 in a tight engagement with one another wherein the at least two stackable layers 60, 62, 64 are adjacent one another and compressed toward one another by the fastener to form a unitary or monolithic construction. The cooperation of fasteners 16 and apertures 36 in this embodiment is advantageous because it facilitates fastening of the at least two stackable layers 60, 62, 64 without resulting bulk or protrusions on an exterior surface of the assembled structures 70, 72, 74. By tight engagement, the stackable layers do not shift relative to one another and are firmly located adjacent one another.

In an embodiment, the at least two stackable layers 60, 62, 64 have a textured surface to aid in securing the at least two stackable layers 60, 62, 64 in the assembled structures 70, 72, 74. The textured surface may have a predetermined surface pattern which functions to interlock with the textured surface of an adjacent stackable layer, controlling range of movement between individual stackable layers. The textured surface may comprise protrusions and indentations randomly formed or in a prearranged pattern. The textured surface may be formed by additives, films, or formed into the stackable layers. In this way, the textured surface may further function to advantageously resist shear forces that the assembled structure may experience during use, enhancing its structural rigidity and facilitating the assembled structure's endurance of transverse and axial forces.

In embodiments where the at least one fastener 16 serves further to adjoin one or more assembled structures in a pivot arrangement, the predetermined surface pattern may be configured to control range of motion of the assembled structures relative to each other, for example by providing one or more stops that limit movement in one or more directions. The at least one fastener 16 may also adjoin one or more assembled structures in a non-moving relationship to each other.

Turning now to FIGS. 10*a* and 10*b*, alternative shapes of the at least two stackable layers are illustrated. FIG. 10*a* shows a tubular assembled structure 66 comprising at least two stackable layers 67 and at least one fastener (not shown). The embodiment of FIG. 10*a* is advantageous in enduring axial forces and is more appropriate as a structural component in certain devices. The at least two stackable layers may be arranged as depicted in FIG. 10*b*, where a U-shaped assembled structure 68 comprising U-shaped stackable layers 69 is shown. Such a configuration may be more suitable as a structural component or support in certain devices and/or provide enhanced endurance of transverse forces. As with stackable layers 60, 62, 64, stackable layers 67, 69 can be adjusted in shape, and when secured by at least one fastener into assembled structures 66, 68, the assembled structures 66, 68 are at least semi-rigid or substantially rigid.

FIG. 11 provides an exploded profile view of the assembled structure 70 comprising at least two stackable layers 60 and at least one fastener 16. The assembled structure 70 may be dis-assembled by releasing the at least one fastener 16 on both sides of the assembled structure 70 and pulling the at least two stackable layers 60 apart from each other. The assembled structure 70 may be reformed, for example after adjusting the shape of the stackable layers 60, by stacking the at least two stackable layers 60 on top of each other and re-affixing the at least one fastener 16.

Figure 12:
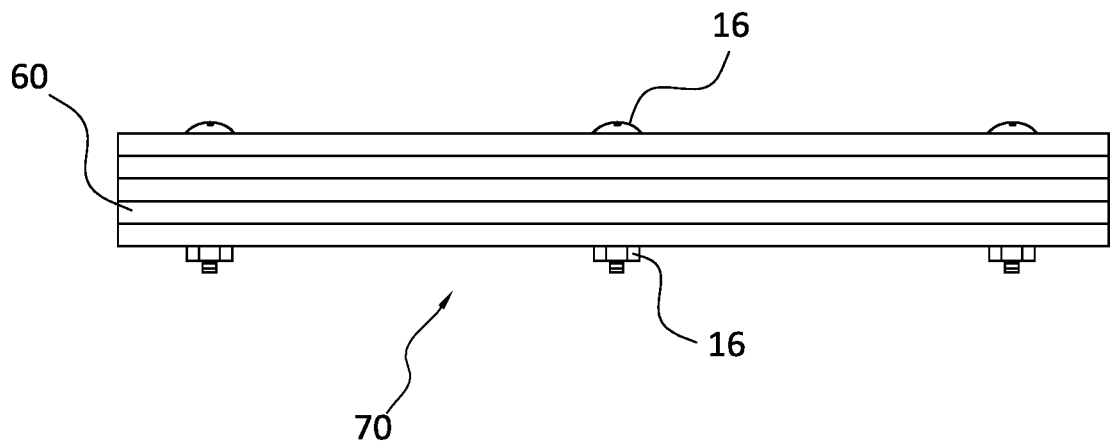
FIG. 12 is an elevational view of the assembled structure depicted in FIG. 11.
Figure 13:
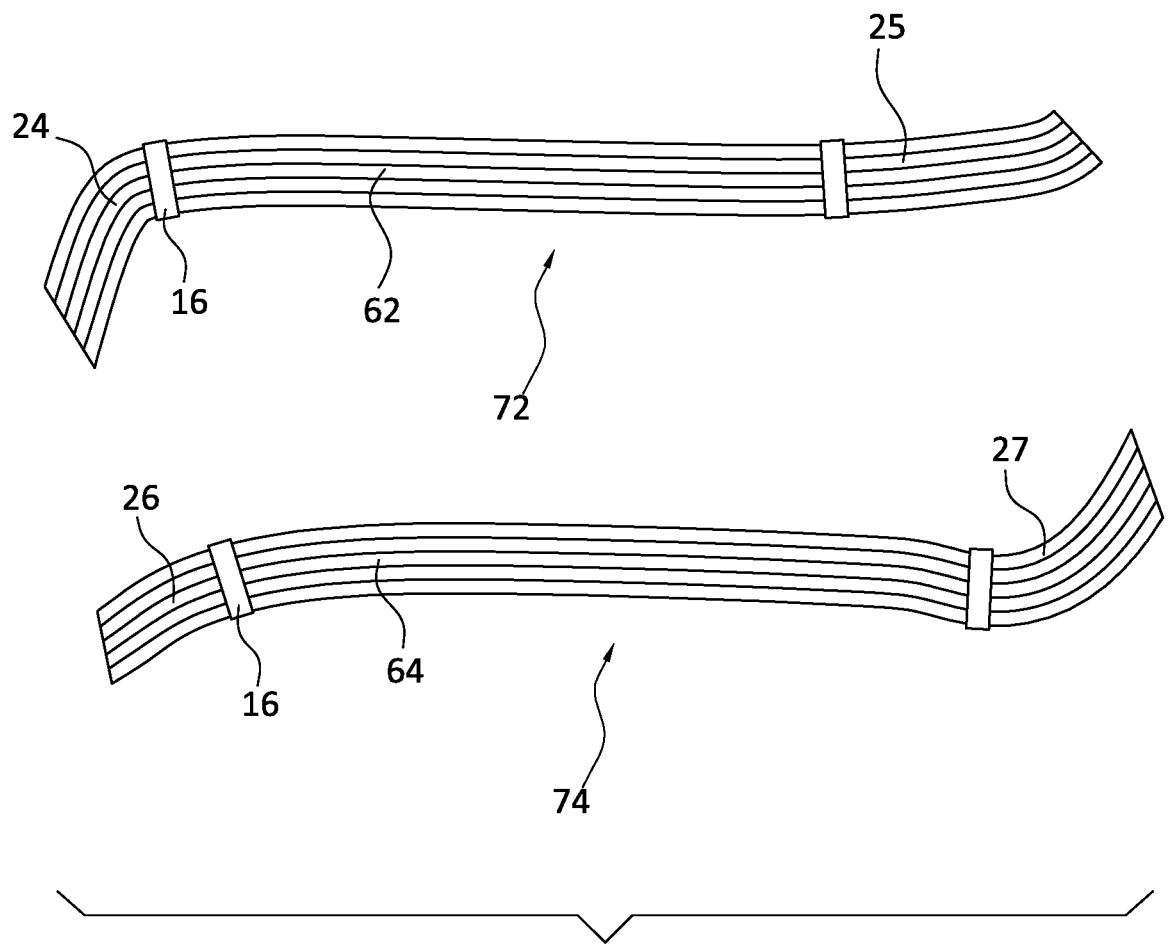
FIG. 13 is an elevational view of assembled structures having different configurations.

FIG. 12 provides an elevational view of the assembled structure 70. The at least two stackable layers 60 are releasably secured by the at least one fastener 16 cooperating with the at least one aperture 36 into the assembled structure 70. FIG. 13 provides an elevational view of the assembled structures 72, 74 comprising stackable layers 62, 64. In this embodiment, the at least one fastener 16 is of the bracket variety, extending around the assembled structures 72, 74 to secure the stackable layers in position.

In another embodiment, the assembled structures 70, 72, 74 may comprise stackable layers comprising different materials. For example, the outermost stackable layers may comprise carbon fiber to provide exterior hardness and support, while the inner layers may comprise cheaper material such as plastic or rubber. Such an arrangement is advantageous because it provides an assembled structure 70, 72, 74 capable of providing required rigidity and adjustability while reducing the costs of manufacturing.

The stackable layers may be permanently fixed into position in the assembled structure. This is desirable where a permanently fixed rigid element is required but the specific dimensions required of the rigid element may not be ascertainable at the time of manufacturing. For example, a clinician may need to provide a rigid crossbar for a knee brace, but the precise dimensions of the user's leg may not be ascertainable outside of a clinical setting. Providing at least two stackable layers that may be adjusted by the clinician to the desired configuration and then fixed into an assembled structure in situ to provide the required rigidity is desirable for avoiding the costs and inconvenience of remote manufacturing of such rigid elements.

After the assembled structure is secured by the at least one fastener, the assembled structure may be permanently fixed into position by a separate process, for example by curing (if the stackable layers comprise carbon fiber or thermoplastic material) or by welding (if the stackable layers comprise metallic material), or through adhesives such as resins. In certain embodiments, after the assembled structure has been permanently fixed into position, the at least one fastener may be removed. These embodiments are advantageous in settings where the rigid structure must be shaped in situ for specific dimensions without the need to be adjusted after the initial fitting.

Figure 14:
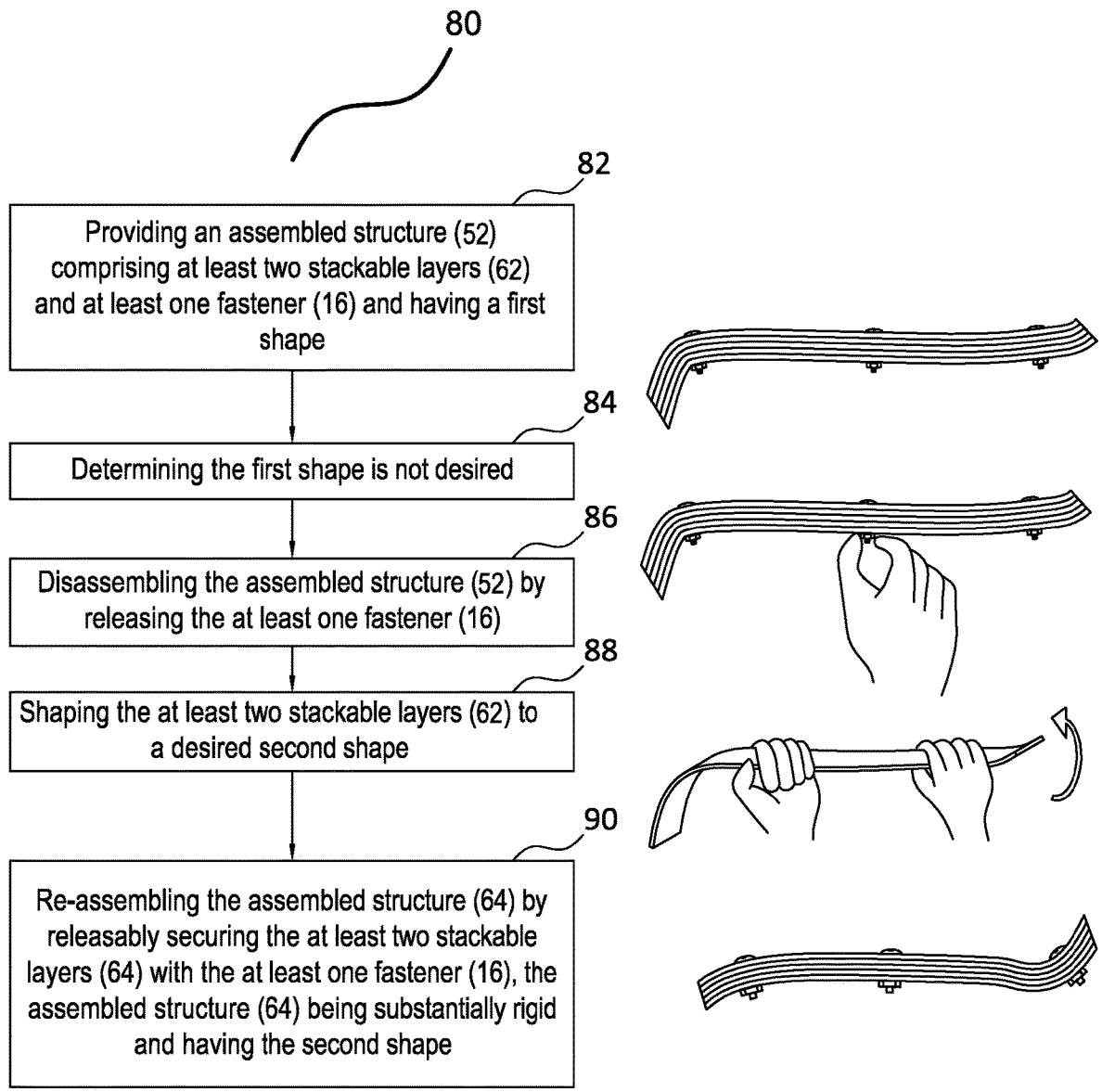
FIG. 14 is a flowchart showing a method for adjusting the shape of an assembled structure with representative images for the steps of the method.

FIG. 14 shows a method 80 for adjusting the shape of an assembled structure comprising stackable layers. The method 80 includes an act 82 of providing an assembled structure in a first shape comprising at least two stackable layers and at least one fastener, the assembled structure having a first shape. For example, the assembled structure may be the assembled structure in the first shape 72 which receives its shape from first and second curvatures 24, 25 and comprises at least two stackable layers 32 and at least one fastener 16.

The method 80 may include an act 84 of determining that the first shape is not desired. For example, the assembled structure in the first shape 72 may have its first and second curvatures 24, 25 because the assembled structure in the first shape 72 underwent mechanical stresses, tensions, or creep, or high temperature changes, resulting in first and second curvatures 24, 25. In another example, a device, structure, element, or machine for which the assembled structure in the first shape 72 was designed and produced to be complementary may have changed in shape or configuration, rendering the assembled structure in the first shape 72 ineffective or obsolete. In these and other possible scenarios, a user may find that the shape of the assembled structure in the first shape 72 is not desirable.

The method 80 may include an act 86 of disassembling the assembled structure by releasing the at least one fastener. For example, if the at least one fastener 16 in the assembled structure in the first shape 72 is of the nuts and bolts variety, a user may release the at least one fastener 16 by appropriately turning the nuts and/or bolts, releasing the at least two stackable layers 62 from the assembled structure in the first shape 72.

The method 80 can include an act 88 of shaping the at least two stackable layers 62 to a desired second shape. For example, a user or practitioner/clinician may adjudge that the assembled structure in the second shape 74 is more appropriate for a specific use. In an embodiment, because the at least two stackable layers in the first shape 62 of the now-disassembled assembled structure in the first shape 72 have properties of being sufficiently pliant to be shapeable by hand, the user or practitioner/clinician shapes each of the at least two stackable layers 62 to add third and fourth curvatures 26, 27 and also remove first and second curvatures 24, 25. The at least two stackable layers in the first shape 62 take the form of the at least two stackable layers in the second shape 64.

Finally, the method 80 includes an act 90 of re-assembling the assembled structure by releasably securing the at least two stackable layers with the at least one fastener, the assembled structure being at least semi-rigid or substantially rigid and having the second shape. For example, if the at least two stackable layers in the second shape 64 comprise at least one aperture 36, the user aligns corresponding apertures 36 on the at least two stackable layers in the second shape 64, threads the at least one fastener 16 through the at least one aperture 36, and then, if the at least one fastener 16 is of the nuts and bolts variety, appropriately turns the nuts and/or bolts, releasably securing the at least two stackable layers in the second shape 64 in the assembled structure in the second shape 74. If the at least one fastener 16 is of the bracket variety, the user affixes the at least one fastener 16 around an entirety of the stacked at least two stackable layers in the second shape 64 to create the assembled structure in the second shape 74.

Figure 15:
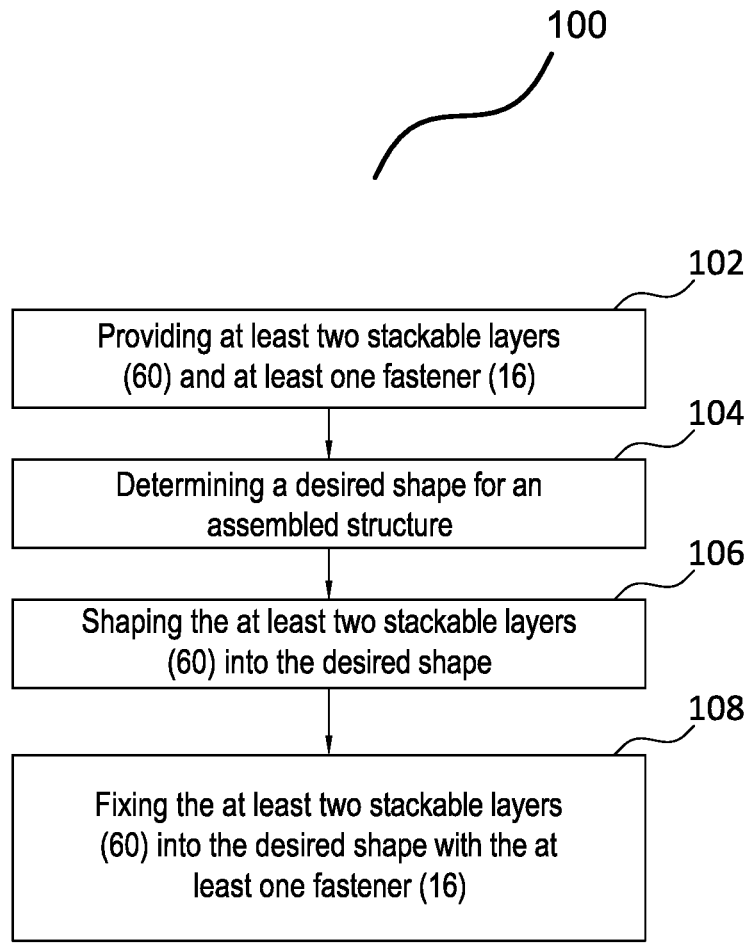
FIG. 15 is a flowchart showing a method for fixing an assembled structure in a desired shape.

FIG. 15 is directed to a method 100 for adjusting the shape of at least two stackable layers to form a rigid element. The method 100 includes a step 102 of providing at least two stackable layers and at least one fastener. At least two stackable layers and at least one fastener can be assembled by a user to form an assembled structure in a desired shape.

The method 110 comprises step 104 of determining a desired shape for an assembled structure. For example, a clinician tasked with providing a rigid crossbar element for a knee brace may ascertain the dimensions of a user's leg to determine the precise shape needed of the assembled structure.

The method 110 further comprises step 106 of shaping the at least two stackable layers into the desired shape. In the example of step 104, owing to the properties of the at least two stackable layers, the clinician or user may shape each of the at least two stackable layers to the shape determined in step 104 in situ without having to incur the costs and inconvenience of custom remote manufacturing.

The method 110 finally comprises step 108 of fixing the at least two stackable layers into the desired shape with the at least one fastener. For example, if the at least one fastener 16 is of the bracket variety, the bracket is fixed around the entirety of the stacked at least two stackable layers 60 to form the assembled structure.

Figure 16:
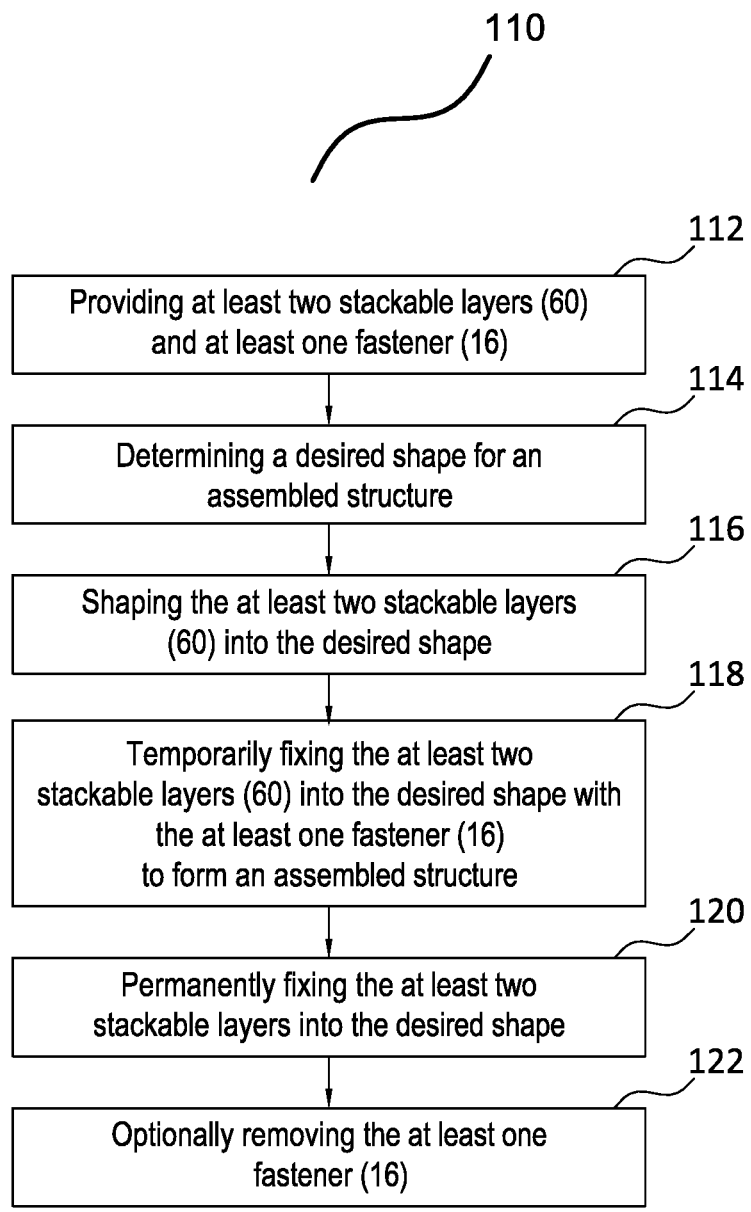
FIG. 16 is a flowchart showing a method for fixing an assembled structure in a desired shape and then removing at least one fastener.

FIG. 16 is directed to a method 110 for adjusting the shape of at least two stackable layers to form a rigid element. The method 110 comprises a step 112 of providing at least two stackable layers and at least one fastener. At least two stackable layers and at least one fastener can be assembled by a user to form an assembled structure in a desired shape.

Method 100 further comprises a step 114 of determining a desired shape for an assembled structure. For example, a clinician tasked with providing a rigid crossbar element for a knee brace may ascertain the dimensions of a user's leg to determine the precise shape needed of the assembled structure.

Method 100 further comprises a step 116 of shaping the at least two stackable layers into the desired shape. In the example above, the clinician or user may shape each of the at least two stackable layers to the shape determined in step 114 in situ without having to incur the costs and inconvenience of custom remote manufacturing.

Method 100 further comprises a step 118 of temporarily fixing the at least two stackable layers into the desired shape with the at least one fastener to form an assembled structure. For example, if the at least one fastener 16 is of the bracket variety, the bracket is fixed around the entirety of the stacked at least two stackable layers 60 to form the assembled structure. If the at least one fastener 16 is of the nuts and bolts variety, at least one aperture 36 in the at least two stackable layers 60 are aligned and the at bolt is threaded through the at least one aperture and secured on an opposite side of the stackable layers 60 by a corresponding nut.

Method 110 further comprises a step 120 of permanently fixing the at least two stackable layers into the desired shape. For example, if the at least two stackable layers 60 comprise thermoplastic material, the at least two stackable layers 60 may be cured; alternatively, if the at least two stackable layers 60 comprise metallic material, the at least two stackable layers 60 may be welded; alternatively, if the at least two stackable layers 60 comprise carbon fiber, the at least two stackable layers 60 may be secured by an adhesive resin.

Method 110 comprises an optional step 122 of removing the at least one fastener 16. For example, if the at least one fastener 16 is of the bracket variety, the brackets may be detached from around the entire assembled structure.

The assembled structure may further comprise attachments or devices between the stackable layers, for example spacers, springs, guides, or other attachments so the assembled structure has additional properties advantageous for specific uses. For example, an assembled structure functioning as a support in a post-operative or therapeutic orthopedic device may feature springs between certain stackable layers to add biasing resistance allowing a user to incrementally develop muscle strength by exerting force against the orthopedic device. The same can be easily and quickly adjusted by a clinician or user to add or remove additional springs to adjust the resistance throughout treatment, owing to the properties of embodiments of the assembled structures described in this disclosure.

The assembled structure comprising stackable layers improves upon existing rigid structures in that it may be adjusted in shape as needed or desired, and it may be adjusted easily and conveniently without specialized machinery and/or complex technical processes. When the assembled structure is used with other devices, it advantageously provides convenient adjustability in response to, for example, changes in configuration of an object for which the devices should fit or be complementary, or in another example, changes in the configuration of the assembled structure due to mechanical and/or temperature effects.

It is understood that while representative embodiments of the disclosure are a prosthetic socket, an ankle foot orthosis, and a temporary splint for an injured arm or shoulder, the assembled structure comprising stackable layers can be adjusted and implemented in not only many prosthetic and orthopedic devices, but also in any devices where a semi-rigid or rigid structure is desired to be adjustable in shape. It is understood by those skilled in the art that the disclosure extends beyond the specifically disclosed representative embodiments to other alternative embodiments and/or uses of the embodiments, and obvious modifications and equivalents thereof. It is intended that the present disclosure should not be limited by the disclosed embodiments described above.

It is to be understood that not necessarily all objects or advantages may be achieved under any embodiment of the disclosure. For example, those skilled in the art will recognize that the assembled structure comprising stackable layers may be embodied or carried out so it achieves or optimizes one advantage or group of advantages as taught herein without necessarily achieving other objects or advantages as taught or suggested herein.

The skilled artisan will recognize the interchangeability of various disclosed features. Besides the variations described, other known equivalents for each feature can be mixed and matched by one of ordinary skill in this art to construct an assembled structure comprising stackable layers under principles of the present disclosure.

The invention claimed is:

1. A structure, comprising:
    first and second stackable layers having properties allowing for the first and second stackable layers to be shaped into at least first and second different shapes, each of the first and second stackable layers being discrete and individual, each of the first and second stackable layers being flexible and resilient such that each of the first and second stackable layers are arranged sufficiently pliant as to be shapeable by hand; and
    at least one fastener to releasably secure the first and second stackable layers together in one of the at least first and second shapes in a semi-rigid or rigid, and unitary construction, wherein the first and second stackable layers are only secured to one another by said at least one fastener;
    wherein the first and second stackable layers are secured into one of the at least first and second shapes by the at least one fastener to form a semi-rigid or rigid, and unitary construction;
    wherein the first and second stackable layers are uniform in size and shape;
    wherein the first and second stackable layers each define first and second apertures each having a same elongate shape through which first and second fasteners of the at least one fastener extend, the first and second apertures of the first stackable layer are arranged at first and second locations along a length thereof corresponding to first and second locations, respectively, of the first and second apertures of the second stackable layer so that the first and second apertures of the first and second stackable layers align with one another, respectively;
    wherein each of the first and second stackable layers is shaped in a sheet-like and elongate form, coextensive with one another;
    wherein for each of the at least first and second shapes, the first and second stackable layers each define a first curvature only defined between the first and second apertures at a third location, and a second curvature only defined between the first aperture and a third aperture at a fourth location, the third and fourth locations being the same for each of the first and second stackable layers;
    wherein the first aperture of each of the first and second stackable layers is located at a middle of the length of the first and second stackable layers, wherein the second and third apertures are located on opposed sides of the first aperture;
    wherein the at least one fastener secures the first and second stackable layers into engagement with each other, said at least one fastener comprising first, second and third bolts and corresponding nuts, securable to the first and second stackable layers and extending entirely through the first, second and third apertures, respectively, of each of the first and second stackable layers such that the first, second and third bolt secure in place the first and second stackable layers into said first and second shapes;
    wherein the first and second stackable layers have a textured surface comprising at least one of protrusions and indentations in a prearranged pattern;
    wherein the structure further comprises at least one cuff secured to the structure by the first fastener and extending laterally relative to the length of the first and second stackable layers;
    wherein the at least one cuff includes first and second cuffs such that the first cuff is located at the first aperture of the first stackable layer and secured at the first location along the length thereof corresponding to first location by the first fastener, and the second cuff is located at the second aperture of the first stackable layer and secured at the second location along the length of the first stackable layer by the second fastener, wherein the second location is located below the first location of the first stackable layer along the length thereof;

wherein the first stackable layer defines proximal and distal ends, the first and second cuffs being located between the proximal and distal ends.

2. The structure of claim 1, wherein rigidity of assembled structure is arranged for being incrementally adjustable by adding a third stackable layer to the first and second stackable layers.

3. The structure of claim 1, wherein at least one of the first and second stackable layers comprises a polymeric material.

4. The structure of claim 1, wherein at least one of the first and second layers defines at least one recess configured in size and shape to receive the at least one fastener.

5. The structure of claim 1, wherein the first and second stackable layers each comprise a predetermined surface pattern configured in size and shape to interact with the surface pattern on an adjacent one of the first and second stackable layers.

6. The structure of claim 5, wherein the textured surface is arranged to control a range of motion between another assembled structure adjoined by the at least one fastener in a pivoting relationship.

7. The structure of claim 1, wherein the at least one fastener is arranged to join a second assembled structure to the assembled structure in a pivoting relationship.

8. The structure of claim 1, further comprising at least one spring device between the first and second stackable layers.

9. The structure of claim 1, further comprising at least one spacer between the first and second stackable layers.

10. A structure, comprising:
    first and second stackable layers having properties allowing for the first and second stackable layers to be shaped into at least first and second different shapes, each of the first and second stackable layers being discrete and individual, each of the first and second stackable layers being flexible and resilient such that each of the first and second stackable layers are arranged sufficiently pliant as to be shapeable by hand; and
    at least one fastener to releasably secure the first and second stackable layers together in one of the at least first and second shapes in a semi-rigid or rigid, and unitary construction, wherein the first and second stackable layers are only secured to one another by said at least one fastener;
    wherein the first and second stackable layers are secured into one of the at least first and second shapes by the at least one fastener to form a semi-rigid or rigid, and unitary construction;
    wherein the first and second stackable layers are coextensive, the first stackable layer having a first predetermined curvature, and the second stackable layer having a second predetermined curvature, the first and second predetermined curvatures being different from one another;
    wherein the first and second stackable layers each define first and second apertures each having a same elongate shape through which first and second fasteners of the at least one fastener extend, the first and second apertures of the first stackable layer are arranged at first and second locations along a length thereof corresponding to first and second locations, respectively, of the first and second apertures of the second stackable layer so that the first and second apertures of the first and second stackable layers align with one another, respectively;
    wherein the first predetermined curvature is defined between the first and second apertures of the first stackable layer, and the second predetermined curvature is defined between the first and second apertures of the second stackable layer;
    wherein the at least one fastener secures the first and second stackable layers into engagement with each other;
    wherein the structure further comprises at least one cuff secured to the structure by the first fastener and extending laterally relative to the length of the first and second stackable layers;
    wherein the at least one cuff includes first and second cuffs such that the first cuff is located at the first aperture of the first stackable layer at the first location along the length thereof corresponding to first location, and the second cuff is located at the second aperture of the first stackable layer at the second location along the length of the first stackable layer, wherein the second location is located below the first location of the first stackable layer along the length thereof;
    wherein the first stackable layer defines proximal and distal ends, the first and second cuffs being located between the proximal and distal ends.

11. The structure of claim 10, wherein the first and second layers have a textured surface comprising at least one of protrusions and indentations in a prearranged pattern.

12. The structure of claim 1, wherein the first curvature at the first location is located between the first and second cuffs.

13. The structure of claim 1, wherein the first cuff has a length that is arranged perpendicular to the length of the first stackable layer, and a height that is parallel to the length of the first stackable layer, the length of the first cuff being longer than the height.

14. The structure of claim 1, wherein the structure defines a third curvature extending from the first aperture to the proximal end of the structure.

15. The structure of claim 10, wherein the first cuff has a length that is arranged perpendicular to the length of the first stackable layer, and a height that is parallel to the length of the first stackable layer, the length of the first cuff being longer than the height.

* * * * *